(12) United States Patent
Colvin, Jr.

(10) Patent No.: US 11,627,728 B2
(45) Date of Patent: Apr. 18, 2023

(54) DEVICES AND METHODS FOR DETERMINING ANALYTES

(71) Applicant: Ryshens Ltd., Tel Aviv (IL)

(72) Inventor: Arthur E. Colvin, Jr., Mt. Airy, MD (US)

(73) Assignee: RYSHENS LTD., Tel Aviv (IL)

( * ) Notice: Subject to any disclaimer, the term of this patent is extended or adjusted under 35 U.S.C. 154(b) by 688 days.

(21) Appl. No.: 16/487,001

(22) PCT Filed: Feb. 23, 2018

(86) PCT No.: PCT/IB2018/000246
§ 371 (c)(1),
(2) Date: Aug. 19, 2019

(87) PCT Pub. No.: WO2018/154389
PCT Pub. Date: Aug. 30, 2018

(65) Prior Publication Data
US 2020/0229402 A1 Jul. 23, 2020

Related U.S. Application Data

(60) Provisional application No. 62/462,556, filed on Feb. 23, 2017.

(51) Int. Cl.
*A01K 45/00* (2006.01)
*G01J 3/44* (2006.01)
(Continued)

(52) U.S. Cl.
CPC .............. *A01K 45/007* (2013.01); *G01J 3/44* (2013.01); *G01N 21/645* (2013.01);
(Continued)

(58) Field of Classification Search
CPC ...... A01K 45/007; G01J 3/44; G01N 21/6428
See application file for complete search history.

(56) References Cited

U.S. PATENT DOCUMENTS

| 5,504,572 A | 4/1996 | Taylor et al. |
| 6,433,293 B1 | 8/2002 | Bollinger et al. |
| (Continued) | | |

FOREIGN PATENT DOCUMENTS

| CN | 202256155 U | 5/2012 |
| JP | 2014-209114 A | 11/2014 |
| (Continued) | | |

OTHER PUBLICATIONS

Supplementary European search report dated Nov. 13, 2020 in connection with European Application No. EP 18 75 7100.
(Continued)

*Primary Examiner* — Hugh Maupin
(74) *Attorney, Agent, or Firm* — Patrick T. Skacel

(57) ABSTRACT

A device for detecting a presence or concentration of an analyte on an egg shell or in an egg, the device comprising an emitter, wherein the emitter is configured to emit light into the egg, a detector, wherein the detector is configured to receive light emitted from an indicator molecule within the egg, a controller configured to analyze a change in a detectable quality of the indicator molecule based on the presence or concentration of the analyte.

26 Claims, 14 Drawing Sheets

(51) Int. Cl.
*G01N 21/64* (2006.01)
*G01N 33/08* (2006.01)
*G01N 21/77* (2006.01)

(52) U.S. Cl.
CPC ....... *G01N 21/6428* (2013.01); *G01N 33/085* (2013.01); *G01N 2021/6432* (2013.01); *G01N 2021/7786* (2013.01)

(56) References Cited

U.S. PATENT DOCUMENTS

| | | |
|---|---|---|
| 6,506,570 B1 | 1/2003 | Phelps |
| 9,241,476 B2 | 1/2016 | Visser |
| 2005/0178689 A1 | 8/2005 | Aardema et al. |
| 2007/0005921 A1 | 3/2007 | Colvin |
| 2008/0200098 A1 | 8/2008 | Moeggenborg et al. |
| 2010/0200596 A1 | 8/2010 | Wallace |
| 2011/0240887 A1 | 10/2011 | Christensen et al. |
| 2012/0058052 A1 | 3/2012 | Decuypere et al. |
| 2014/0099265 A1 | 4/2014 | Decuypere et al. |
| 2014/0296707 A1 | 10/2014 | Massonneau et al. |
| 2015/0125347 A1 | 5/2015 | Machuca |
| 2015/0138535 A1 | 5/2015 | Walukas et al. |
| 2016/0374556 A1 | 12/2016 | Colvin |

FOREIGN PATENT DOCUMENTS

| | | | |
|---|---|---|---|
| WO | WO 2004/023136 A2 | 3/2004 | |
| WO | WO-2009055702 A1 * | 4/2009 | ............ G01N 21/783 |
| WO | WO-2011071551 A1 * | 6/2011 | ........ B01L 3/502715 |
| WO | WO 2016/005539 A1 | 1/2016 | |
| WO | WO 2016/083416 | 6/2016 | |

OTHER PUBLICATIONS

Dec. 1, 2020 Written Opinion issued in connection with European Application No. EP 18 75 7100.
International Preliminary Report on Patentability for PCT App. No. PCT/IB21018/000246 dated Jun. 18, 2018.
Search Report and Written Opinion for PCT App. No. PCT/ib2018/000246 dated Jun. 18, 2018.
Examiner's Report dated Sep. 1, 2022 in connection with European Application No. EP 18 757 100.5.

* cited by examiner

DEVICES AND METHODS FOR DETERMINING ANALYTES

CROSS REFERENCE TO RELATED APPLICATIONS

The present application claims the benefit of U.S. Provisional Application No. 62/462,556, filed Feb. 23, 2017, which is incorporated herein by reference in its entirety for all purposes under the law.

FIELD OF THE INVENTION

The present invention provides a system that may be used for determining analytes in materials, such as eggs.

BACKGROUND OF THE INVENTION

Chickens and eggs produced by chickens are a major world food source. The UN's Food and Agricultural Organization found 19.5 billion chickens, producing 1.1 trillion eggs annually. ref: http://www.progressive-economy.org/trade_facts/world-chicken-egg-output-1-1-trillion-per-year/

In 2013, world hen egg production is estimated at 68.3 million metric tons and increasing at a rate of between 2-3% annually.

Egg production is portioned to that destined for human consumption of eggs as food products, and eggs for hatching into hens which may be consumed for meat, or eggs for hatching into egg-laying hens for continued egg production.

The global production of broiler meat is around 89.7 million tons. ref: United States Department of Agriculture National Agricultural Statistics Service ISSN: 1949-1476/ Hatchery Production 2015 Summary April 2016.

This weight is produced by an estimated 70 billion chickens which hatch from an initial number of 100 billion eggs each year (based on chicken weight of 2.2 kg, 6% mortality rate and 70% fertility of eggs).

Male chicks born to egg-laying hens cannot lay eggs, and are not the breed used for meat. Therefore, hatcheries separate males from females through a process known as "sexing." Because males are worthless to the egg industry, they are disposed of immediately following hatch and manual sexing. These disposed males are typically ground up in large industrial macerators. Although routine in poultry production, and under existing capability without a reasonable alternative within the market, the mass killing of male baby chicks is considered by many to be unethical and causes much concern particularly within the animal rights community. It is also very economically inefficient in that 50% of the egg crop converted to product as meat or layers is destroyed.

The global egg industry destroys about 6,000,000,000 newborn male chicks every year. (ref: http.//freefromharm.org/eggfacts)

In the current process, eggs are laid by the producing hen stock and the eggs must be cared for and incubated under tightly controlled hatchery conditions for rotation, temperature, humidity, protection from infection and pathogens, etc., for a period of 22 days required for the eggs to hatch. The cost of the existing method includes not only the inefficiency of ultimately destroying 50% of hatchlings, but also the operating costs of the hatchery during the 22 days to care for the full number of eggs, and the cost of many assembly line human trained "chick sexers" to sort the males from females.

Only after the egg has hatched is it possible with today's technology which requires that each chick following hatch being picked up and manually inspected and sorted into males (to be destroyed) and females which will be grown out as meat or egg producers. All existing methods of manually determining chick sex require individual handling following the 28-day incubation period for each egg produced. An individual must also be trained extensively to be able to determine the sex of a chick at hatch.

The sexing cost is different for layers and broilers. Layers are sexed by the expensive bib method which costs 5-10 cents per chicken while broilers are mostly sexed by the feathers color method which is about 2 cents per chick.

The Broiler IN OVO sexing market is much greater than the Layers market (100 billion eggs vs. 10 billion layers eggs). Broilers are sexed post hatching by only 25% of US hatcheries, and much less globally. Broilers are sexed but the males are not necessarily being destroyed. Mostly they are segregated and raised in separated flocks under special feeding regimes. Most sexing is based on feathers' color. The process is 85% accurate and costs approx. 2 cents per chick.

There is a need for a less expensive and more accurate non-harming in-ovo sexing method to serve a substantial market potential (1 billion US$ per year, based on 100 billion eggs at 1 cent /egg) for in-ovo sexing.

SUMMARY OF THE INVENTION

In accordance with one embodiment of the invention, a device for detecting a presence or concentration of an analyte in an egg is provided comprising an emitter, wherein the emitter is configured to emit light into the egg, a detector, wherein the detector is configured to detect light emitted from an indicator molecule in the egg, a device body configured to hold the detector and the emitter in the vicinity of the egg, and a controller configured to analyze a change in a detectable quality of the indicator molecule based on the presence or concentration of the analyte.

The device body can have an enclosed chamber configured to encase the egg. The enclosed chamber can have an outer housing comprised of a polymer and an inner liner comprised of aluminum with a mirror polish. The device body can also be an open cylinder configured to surround the egg, or a hand-held wand configured to allow a user to position the emitter and the detector to a position at an outer surface of the egg to perform the detection. The controller can be a computer, the emitter can comprise a light emitting diode, and the detector can comprise a silicon photomultiplier. The detectable quality can be a photoluminescent property, and the analyte can be located on an outer surface of the egg.

In another exemplary embodiment of the invention, a method for detecting a presence or concentration of an analyte in an egg is provided comprising introducing into the egg an indicator molecule having a detectable quality that changes when the indicator molecule is exposed to the analyte, and measuring any change in the detectable quality to thereby determine the presence or concentration of the analyte in the egg.

The indicator molecule can be photoluminescent and the detectable quality that changes can be a change in intensity, luminescent lifetime, a wavelength shift or quenching. The indicator molecule in the egg can be exposed to one or more wavelengths of light matched to the absorbance of the indicator from a light source, and the indicator molecule can emit a luminescent signal after the exposure. The emitted luminescent signal is detected by at least one detector, and the light source comprises a light emitting diode, and the at least one detector comprises a silicon photomultiplier. The presence or concentration of the analyte can be used to determine a condition comprising sex, health, or viral status, and the analyte can be located on an outer surface of the egg.

The above and other various aspects and embodiments are described below with reference to the accompanying drawings.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein.

In the drawings, like reference numbers indicate identical or functionally similar elements.

DETAILED DESCRIPTION OF THE INVENTION

Figure 1:
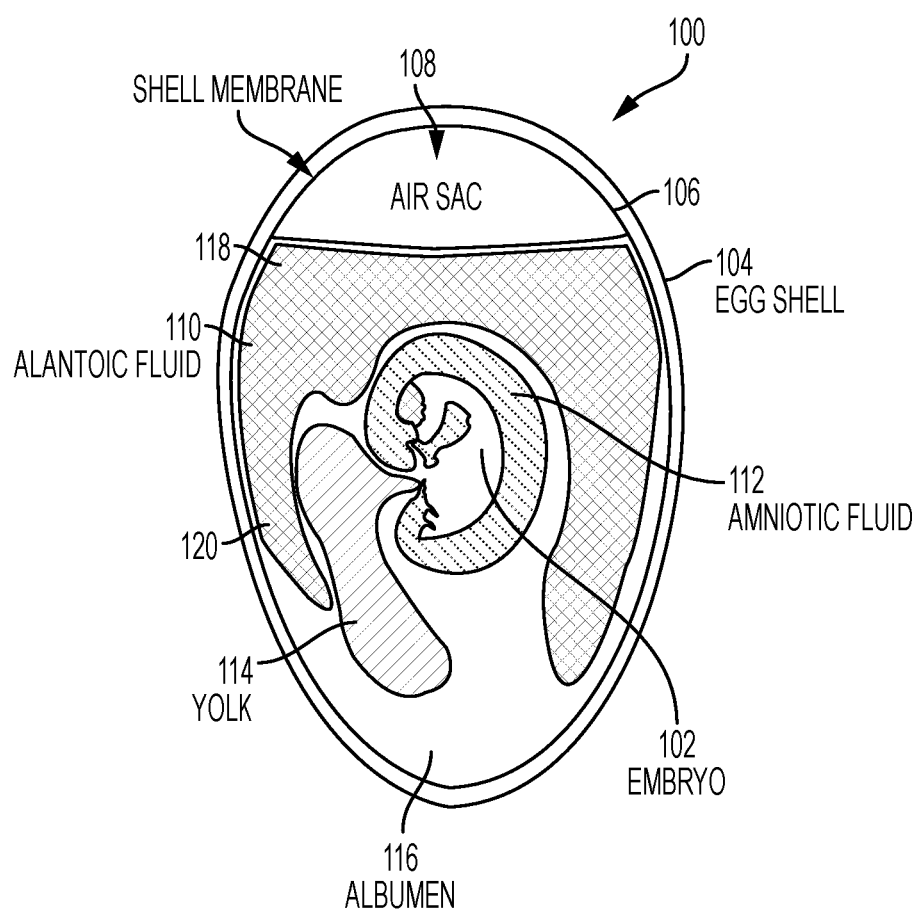
FIG. 1 illustrates aspects of an egg to be analyzed under the devices and methods shown and described herein.

Referring to FIG. 1, a fertilized chicken egg 100 is provided. The egg 100 comprises, among other things, a shell 104, a shell membrane 106, an air sac 108, alantoic fluid 110, amniotic fluid 112, an embryo 102, yolk 114, an albumen 116, an alantoic sac 118, and an chorio-alantoic membrane 120.

A female chicken embryo 102 in the fertilized egg 100 carries a W chromosome which encodes special sequences for specialized enzymes that drive the production and increased concentration of female hormones in the circulating blood, during embryonic development.

Expression of hormones may start even before the start of incubation when the embryo 102 comprises of several hundreds of cells as a germination disc which await incubation.

Metabolic products of female hormones are found in the alantoic fluid 110 within the egg 100 which starts to accumulate on day 5 of the incubation in the newly formed alantoic sac 118.

The female embryo 102 produces much more estrogens that the male embryo. Thus the alantoic fluid 110 of a female embryo contains an approximate 10 fold higher concentration of estrogen conjugates (such as estradiol sulfate, estradiol b17, estrone sulfate, estrone glucuronide, etc.) starting on day 8 of the incubation.

An indicator may be configured for one or more (other) of these markers, or markers for other analytes of interest such as health, nutrition, or disease state or presence indicators.

The alantoic fluid 110 and its chorio-alantoic membrane 120 can serve as a growth medium for viral and bacterial contaminations including several endemic chicken viruses like the NDV and CLV.

Sexing of females based on estrogen conjugates concentration is feasible as of the 8th day through the incubation. The chemical information is within the alantoic fluid 110 to determine whether it will hatch as a male or female by targeting and measuring the concentration of one or more of these chemical markers.

Viral and microbial contamination may be present on the egg shell and in the egg 100 immediately post laying and can be ascertained at any incubation day before hatching.

It will be understood that although a chicken egg is provided as the subject of the analyses as described herein, eggs from other animals can also be analyzed in accordance with the present invention.

Figure 2:
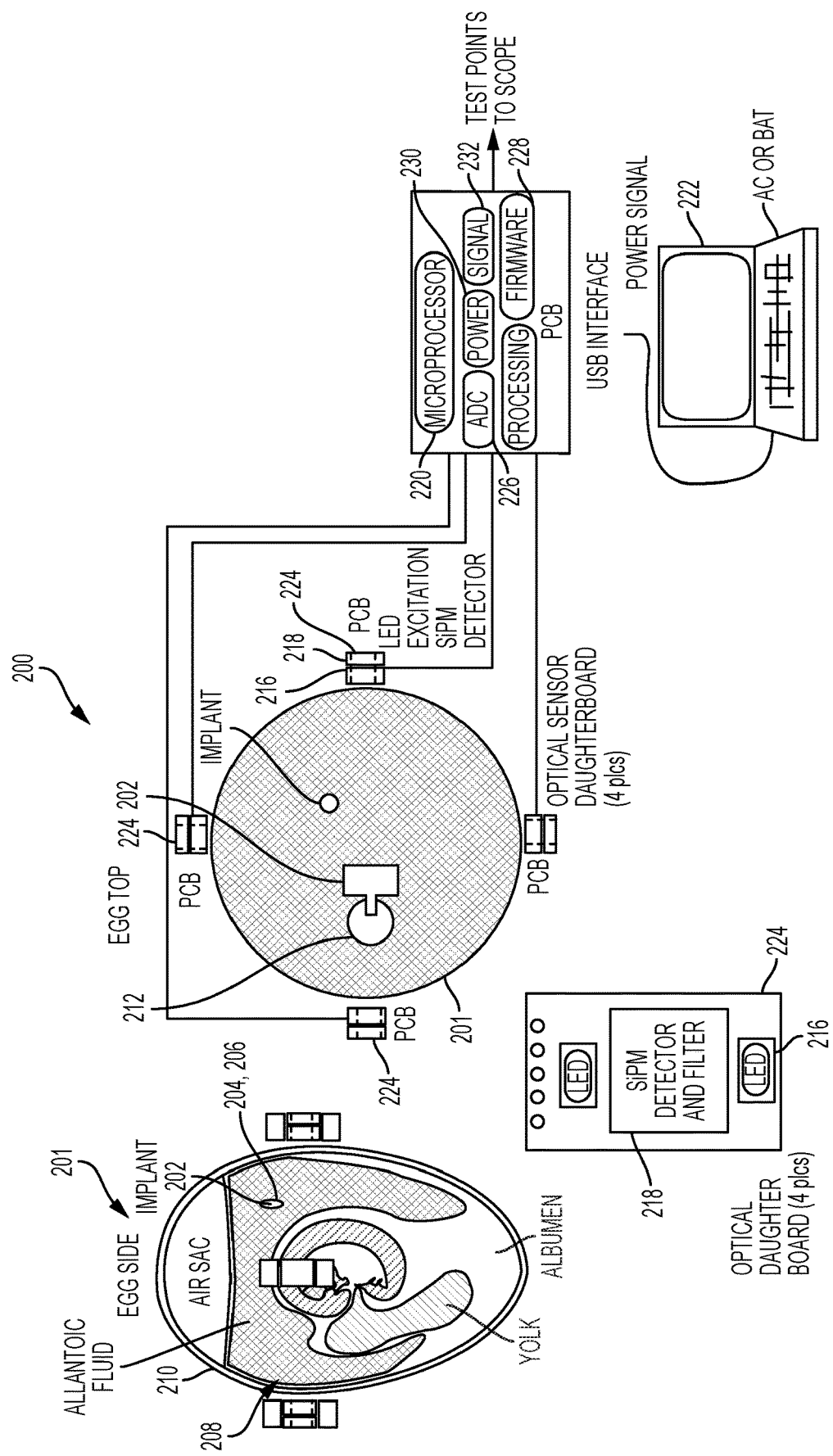
FIG. 2 illustrates an aspect of a device for determining analytes as shown and described herein.

Referring to FIG. 2, in one embodiment, the invention is comprised of an optical reader system 200 that can detect a signal from within an egg 201 generated by at least one indicator 202.

In this embodiment, the indicator 202 may include one or more small (50-500 microns) hydrogel pellets 204 or rods 206 (can be microparticle, nanoparticle, or reagent) that is injected into the egg on days 1-17 after laying through a small hole 208 placed in the egg and resealed with an appropriate sealant 210 (which can be done by a specially designed or modified automated egg injector (modified ID injector needle to fit particle or implant) as may be used by others to introduce typical protective vaccines into an egg within the hatchery system). The identity of the sealant is not critical, and one of ordinary skill would readily identify suitable sealants (e.g., waxes, hot melt adhesives, and other sealants effective at sealing the hole on the egg).

Within the tiny hydrogel body 204 is a photoluminescent indicator 202 which reacts or otherwise responds to the target molecule 212 or molecules by a change in luminescent properties such as intensity, luminescent lifetime, wavelength shift, quenching, or other photoluminescent property.

It will be understood that while hydrogel is disclosed herein, any number of other approaches for delivering an indicator on or within an egg may be used, including, but not limited to, provision of one or more free indicator molecules on or within the egg (e.g. within the alantoic fluid).

The system 200 includes one or more excitation sources (emitters) 216 of one or more wavelengths matched to the absorbance of the indicator 202 injected within the egg, and one or more detectors 218 of one or more emission wavelengths for receiving and measuring the luminescence emitted from the indicator within the egg.

The emitter 216 can be a light emitting diode and the detector 218 can be a silicon photomultiplier, with each component combined with an optical daughter-board 223 to form an optical sensing module 224, with each of four optical sensing modules 224 set at 90 degree intervals surrounding the lateral circumference of the egg (see, e.g., FIG. 3) as the egg is positioned vertically for analysis.

The luminescent signal from the optical sensing modules 224 are interpreted by an algorithm contained within an onboard microprocessor 220, or can be from within a host control computer 222, where the level of signal resulting from change in photo properties of the hydrogel indicator implant within the egg in response to any indicating target molecule(s) 212.

Figure 3:
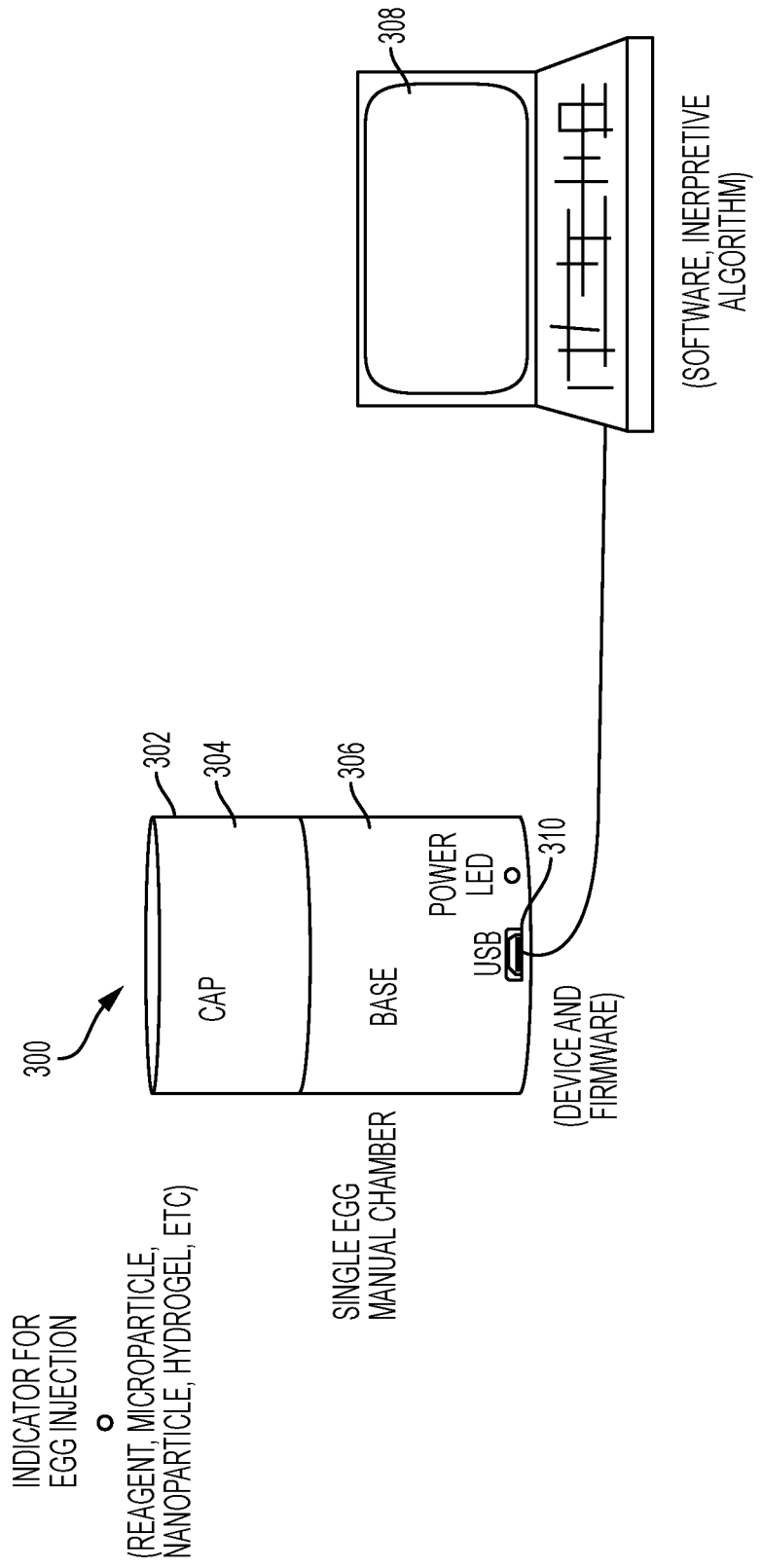
FIG. 3 illustrates another aspect of a device for determining analytes as shown and described herein.

Referring to FIG. 3, the optical reader system 300 may include a chamber 302 in which an egg can be placed inside the chamber manually. In this embodiment, the chamber 302 comprises a cap 304, a base 306, and one or more optical sensing modules 224 with emitters 216 and detectors 218, and is configured so the input and output of the optical sensing modules 224 connect to a laptop 308 or other computing device through a USB 310 or other port or connection.

Figure 4:
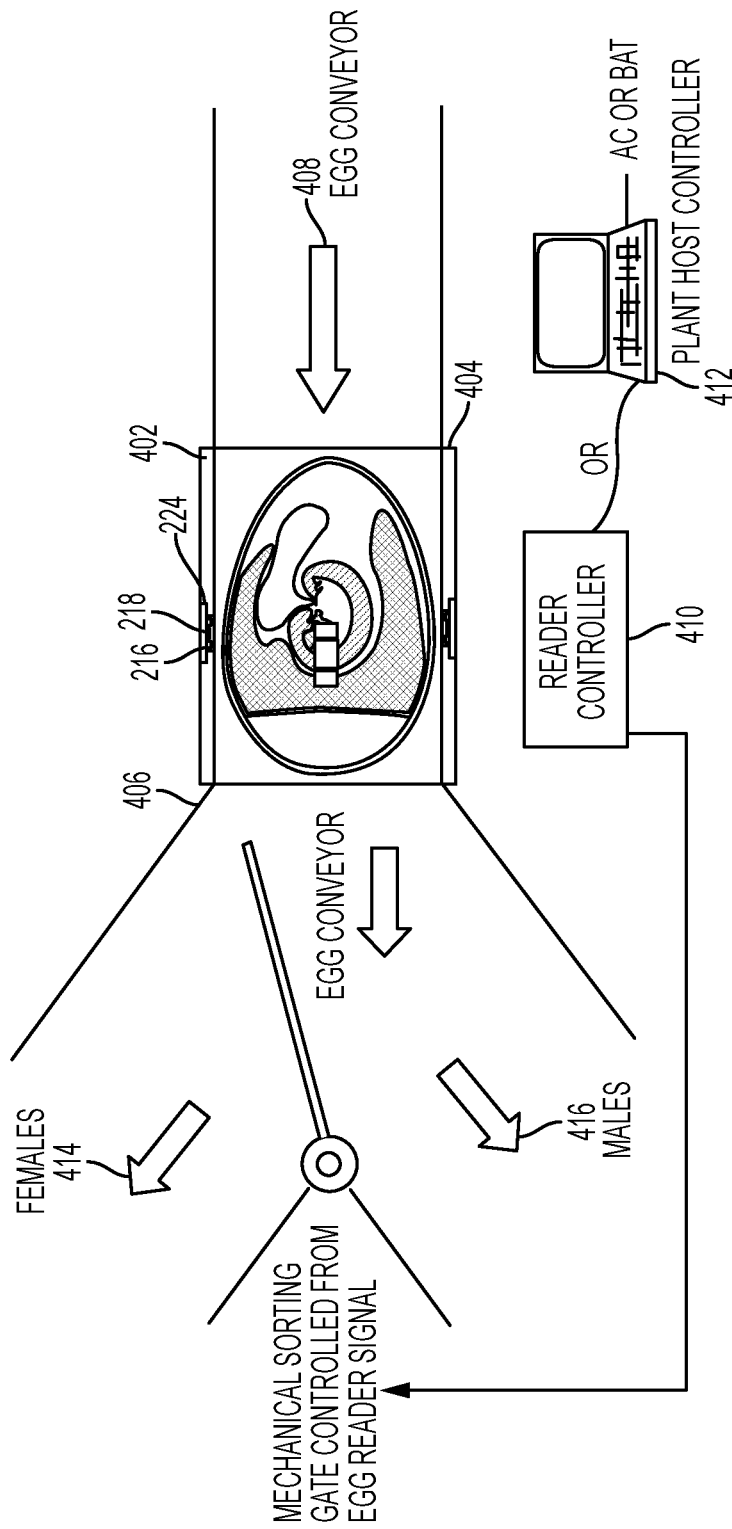
FIG. 4 illustrates another aspect of a device for determining analytes as shown and described herein.

Referring to FIG. 4, the optical reader may also be a pass-through cylindrical chamber 402, open at each end 404, 406, with one or more optical sensing modules 224 with emitters 216 and detectors 218. The pass-through chamber 402 is configured to allow eggs to pass through the chamber 402 via a high speed automated feeding conveyor system 408 for analysis. The optical sensing modules 224 in this embodiment communicates the data to the reader controller 410 and/or plant host controller 412, and the reader controller 410 and/or plant host controller 412 controls mechanical sorting via separate conveyor assemblies based on the egg reader signal. As shown in FIG. 4, in this embodiment, eggs are analyzed for sex and female eggs are sorted on a conveyor to the right 414 and male eggs are sorted on a separate conveyor to the left 416.

Figure 5:
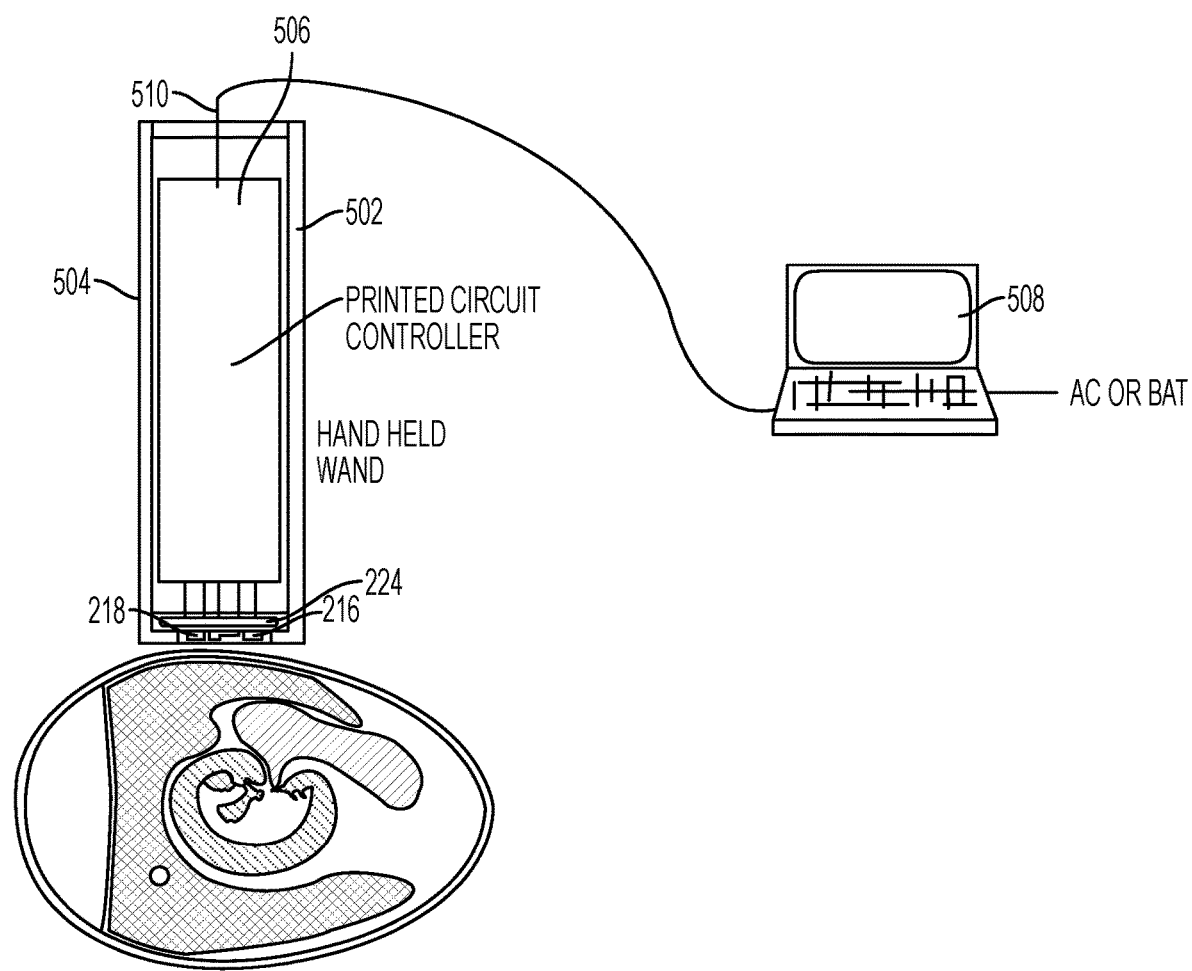
FIG. 5 illustrates another aspect of a device for determining analytes as shown and described herein.

Referring to FIG. 5, the reader may also be configured as a wand or non-chamber shell surface contact reader 502 providing both excitation and detection with filtering that may be used by human inspectors or users or robotic configurations within the hatchery. This reader comprises a hand-held wand body 504 containing a printed circuit controller 506 that receives signals from one or more optical sensing modules 224 with emitters 216 and detectors 218, and is configured so the input and output of the optical sensing modules 224 and printed circuit controller 506 connect to a laptop 508 or other computing device through a USB 510 or other port or connection.

Biological characteristics tested by the system 200 in all embodiments can include sex, health, bacteria, virus, and/or other biological factors and is interpreted into a designation of male or female, fertile or non-fertile, alive or dead, healthy or sick, and the like. Changes in luminescent properties may include lifetime, intensity, wavelength shift, quenching, or other characteristics.

Referring back to FIG. 2, the reader system 200 is configured to provide a non-invasive, high speed (one second or less), automated measurement of an analyte proportional signal from within an egg expected within the alantoic fluid 110 (but can be anywhere within the egg).

The system 200 measures luminescent lifetime from within an egg emitted from an indicator material (or molecule) 202 with an expected lifetime range of ~100 to ~300 microseconds as typical for, e.g., porphyrin based indicators.

Any chromophore with a wavelength that is transmissive through egg shell 104 with a detectable modulation to the target analyte can be measured and serve as indicator 202. Long lifetime (microseconds) NIR type chromophores are preferred. Short lifetime (nanoseconds) chromophores at other wavelengths such as visible range may also be configurable within this device.

Eggs may be hand loaded in and out of the device with read queries made on command from a standard computing device, such as a lap top computer 222. Measurement data may be displayed on the laptop 222.

In this embodiment, the optical design excites the full contents of the egg from four optical sensing modules 224 or pods 224 placed at approximately 90 degrees surrounding the egg containing a total of eight 630 nm LEDS 216 pulsed simultaneously, with return signal captured from four SiPM detectors 218 (silicon photomultiplier chips).

Following LED pulse turnoff, the analog to digital convertor (ADC) 226 on the onboard microprocessor 220 will sample the detectors (sum) at appropriate microsecond intervals (e.g., approximately 5 to 20 microseconds) to measure the first order decay function, and from this data the microcontroller (firmware) 228 will derive and report the decay time. In this embodiment, decay time represents the time it takes the initial excited state signal amplitude (Io) to drop to a value equal to 1/e of Io along the first order of decay. The onboard microprocessor 220 also includes power 230 and signal processing 232 components.

Since naturally occurring and auto-fluorescence occurs in the nanoseconds time range, only the signal from the implant 202 will be detected and measured. Concentration of analyte will be a function of decay time expected ranging between about 100 and 300 microseconds.

Figure 6:
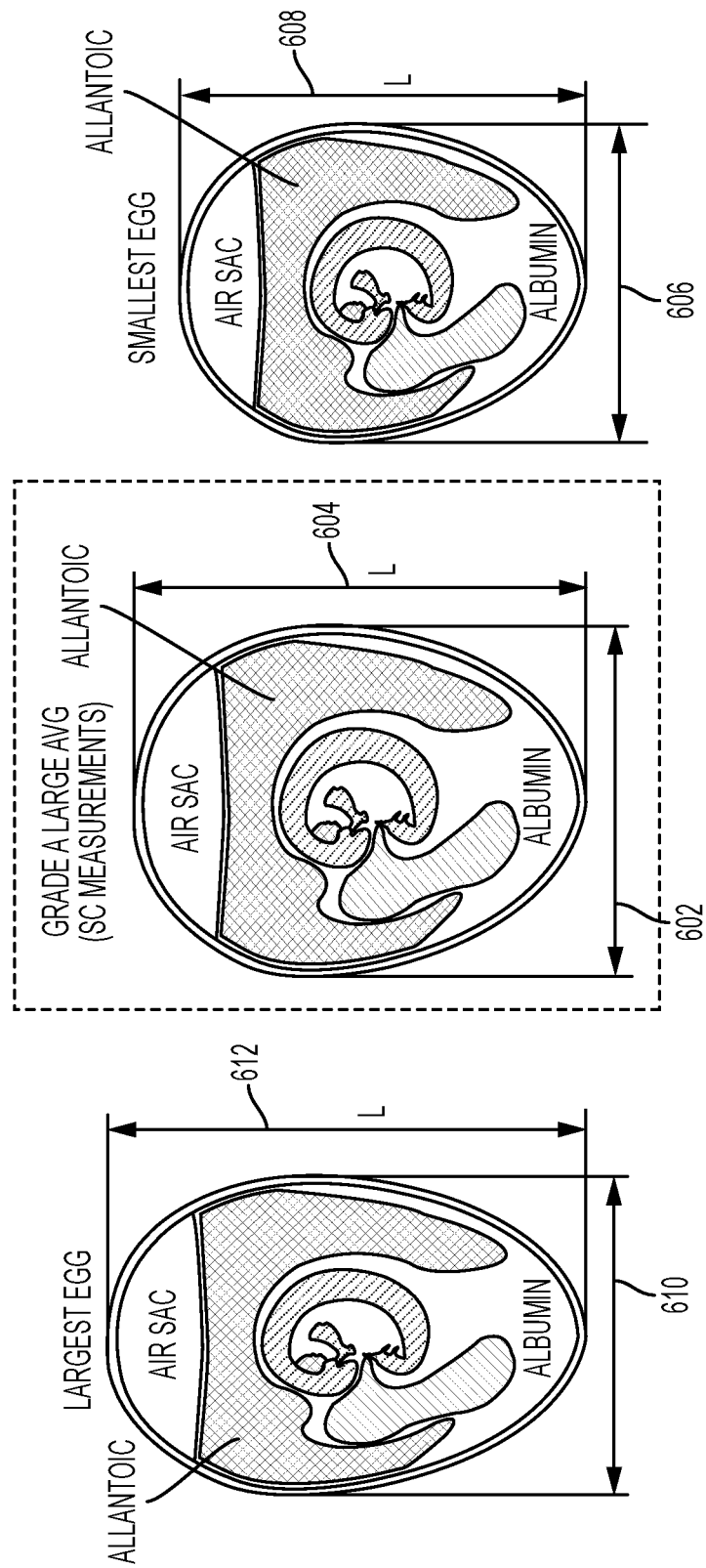
FIG. 6 illustrates aspects of various eggs to be analyzed under the devices and methods shown and described herein.

Referring now to FIG. 6, with respect to chicken eggs, hen egg size can vary. For example, an average Grade A large egg can be 1.77 inches wide 602 and 2.29 inches long 604. A smallest egg can be 1.61 inches wide 606 and 2.04 inches long 608. A largest egg can be 1.85 inches wide 610 and 2.36 inches long 612. Accordingly, a preferred embodiment of a closed chamber design accounts for the largest egg dimension.

Figure 7:
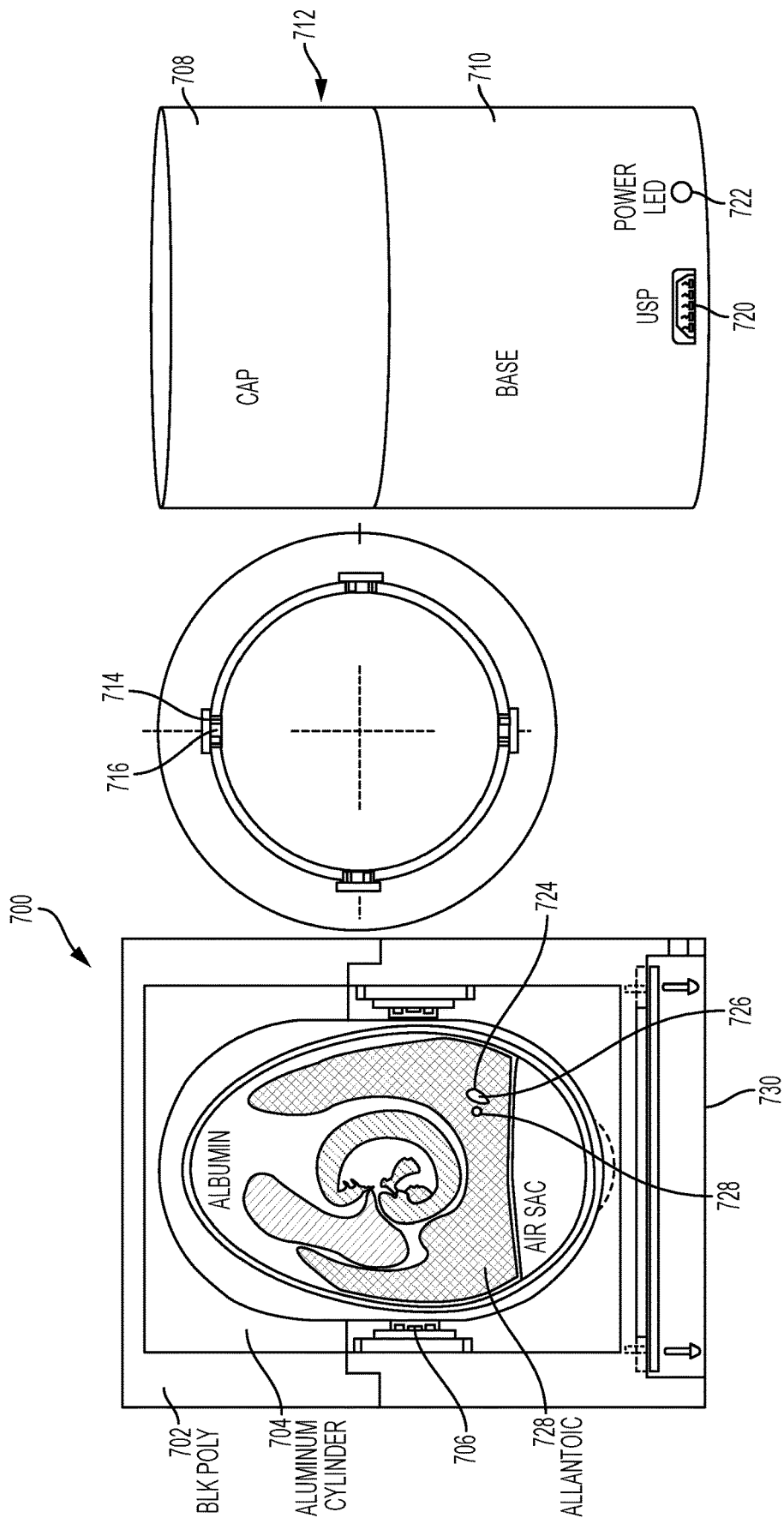
FIG. 7 illustrates another aspect of a device for determining analytes as shown and described herein.

Referring now to FIG. 7, further description of a closed chamber reader 700 is provided. The reader 700 has a light tight black polymer outer housing 702 sized to hold a metal inner liner reflector 704 (with the metal being, for example, aluminum) with a mirror polish on the inside sized to hold the largest egg. Four detector/emitter arrays 706 (e.g., optical sensing modules) each surround the egg spaced at 90 degrees. The reader chamber 712 also comprises a cap 708 and base 710.

The reader 700 is configured to pulse excitation light at 630 nm (or suitable wavelength) from 8 LEDs 714 (4 arrays of 2 each) and detect return luminescence in one or more detectors 716 (Silicon photomultiplier MicroFC-30035-SMT-TA (SiPM), sensL, Cork, Ireland), from an indicator 726 in an implant 724 within the egg injected into the egg 2-4 days prior, with the indicator 726 molecule designed to respond to chicken sex hormone levels and determine whether the egg is male or female based on concentration of the target molecule 728 expressed by decay time or luminescence intensity captured from the 4 each 90 degree spaced SiPM detectors 716.

The detectors may be filtered by Schott RG710 or other cutoff designations as typically available from Edmund Optics, Barrington, N.J. The printed circuit board controller 730 (Nordic Semiconductor NRF52832, Oslo, Norway) is mounted in the base of the chamber and receives power from and provides signal to a laptop via USB port 720 at the chamber base 710. Optionally, the system may include a power LED 722 indicating the chamber 712 is receiving power from the laptop.

Figure 8:
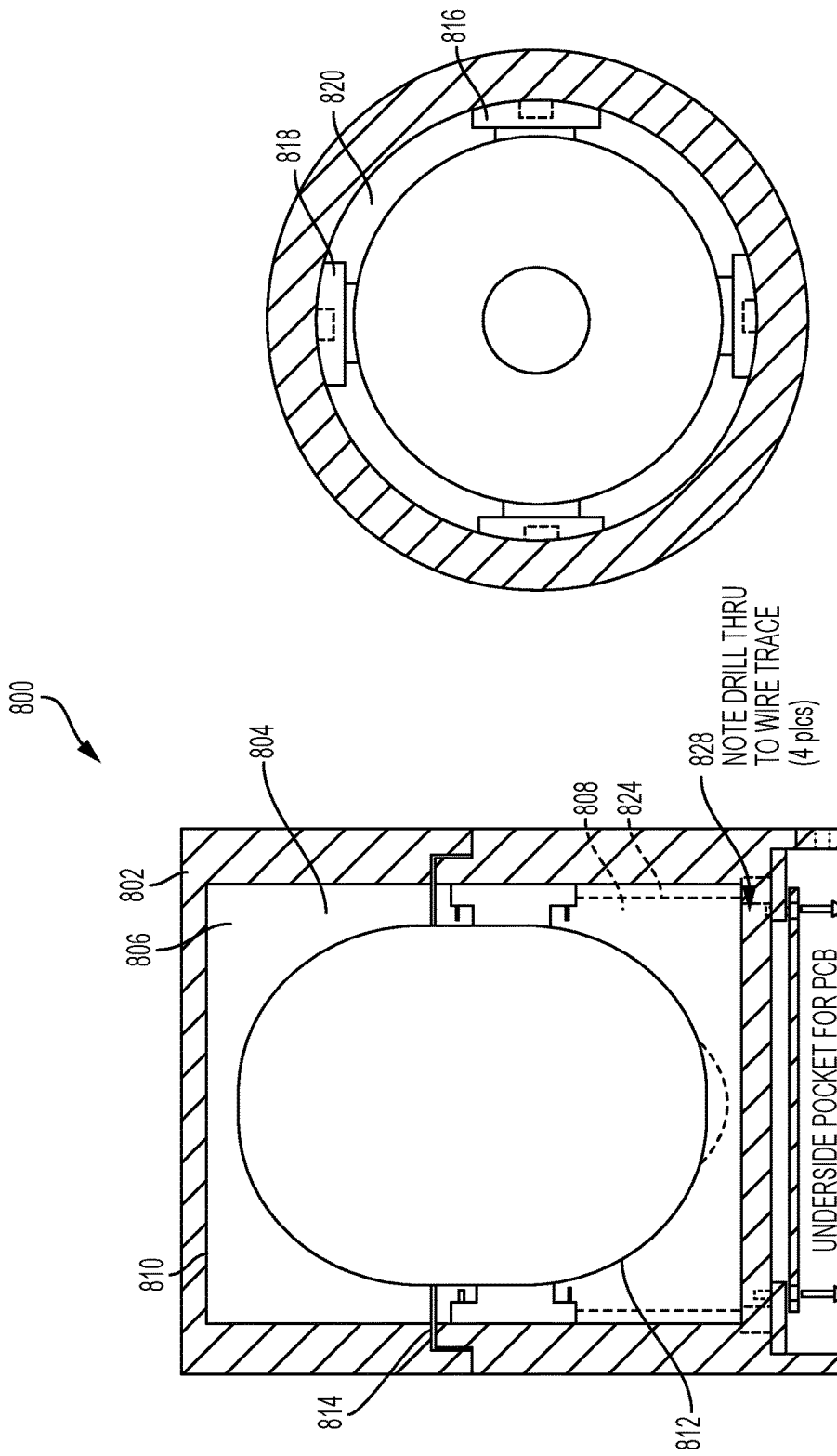
FIG. 8A illustrates another aspect of a device for determining analytes as shown and described herein.
FIG. 8B illustrates another aspect of a device for determining analytes as shown and described herein.

Referring now to FIGS. 8A and 8B, further description of a closed chamber reader 800 is provided. FIG. 8A is a side view and FIG. 8B is a top view. The reader 800 has a polymer outer housing 802. The outer housing 802 surrounds the insert 804. The insert 804 is sized to hold the largest egg dimension, and has a mirror polish on its inner surface 812 and a tool finish on its outer surface 810.

The reader 800 has a cap 806 and a base 808, able to be separated along a top and bottom seam or joint 814. The insert 804 has insets 818 in its cylinder walls 820 configured to hold four detector/emitter arrays 816 spaced at 90 degrees surrounding the circumference of egg.

The reader 800 also has an underside pocket 822 to hold a printed circuit board controller 826. The insert 804 has holes or slots 824 for wires to trace from each detector/emitter arrays 816 for connection to the printed circuit board controller 826.

Similarly, the housing 802 has holes or slots 828 for wires to trace from each detector/emitter arrays 816 for connection to the printed circuit board controller 826. The insert holes 824 and housing holes 828 are configured to line up with each other to allow wires to trace from each detector/emitter arrays 816 for connection to the printed circuit board controller 826. The insert also has an egg divit 830 for securing the egg in position.

Figure 9:
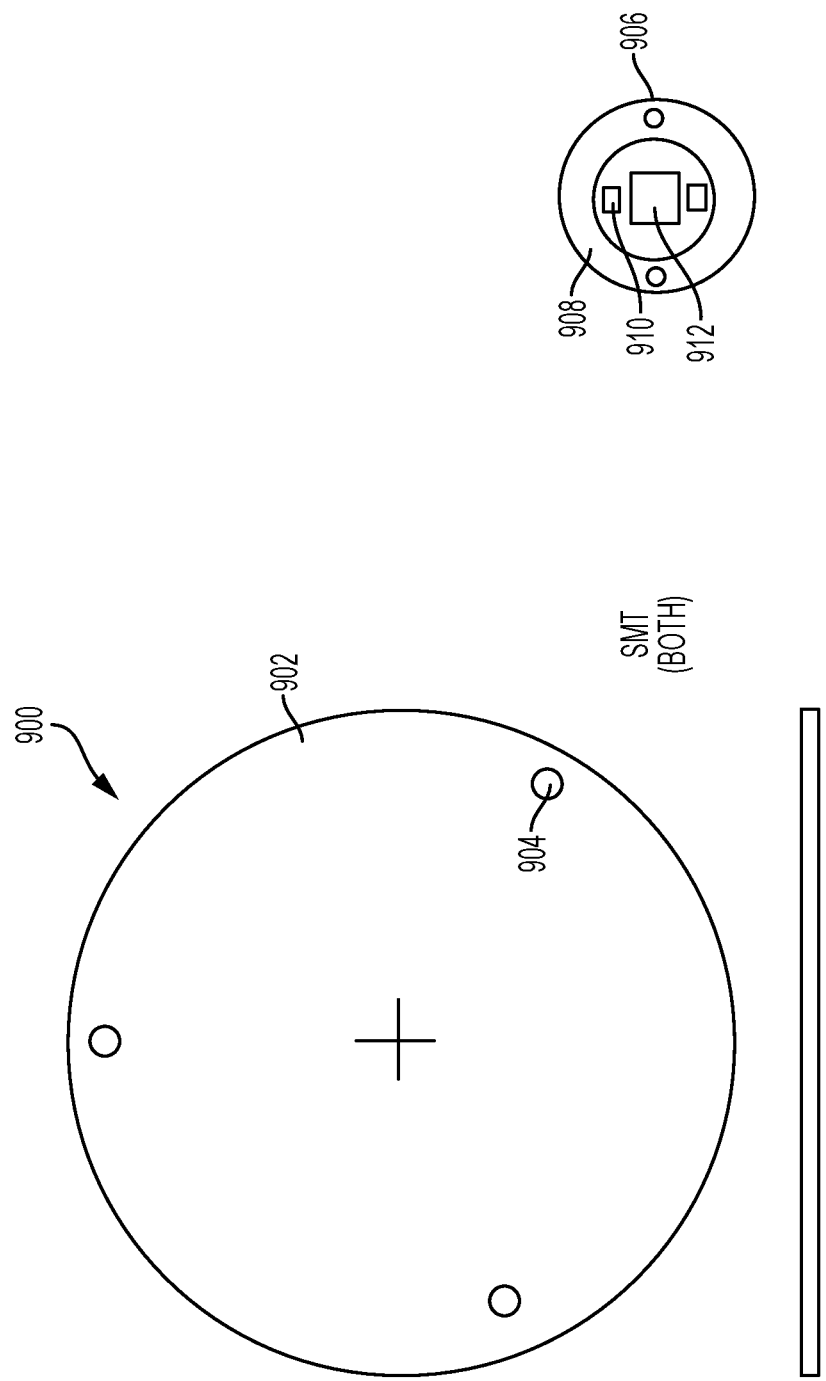
FIG. 9A illustrates another aspect of a device for determining analytes as shown and described herein.
FIG. 9B illustrates another aspect of a device for determining analytes as shown and described herein.

Referring now to FIG. 9A, further aspects of a printed circuit board controller 900 is provided. In this embodiment, the controller 900 is in the form of a flat plate 902 with holes 904 for mounting to the base of the reader 800. The controller is configured to receive wires 906 and signals from the optical sensing modules 908 (FIG. 9B) mounted in the reader as shown and described herein. The optical sensing modules 908 contain LEDs 910 and detectors 912 as shown and described herein.

Figure 10:
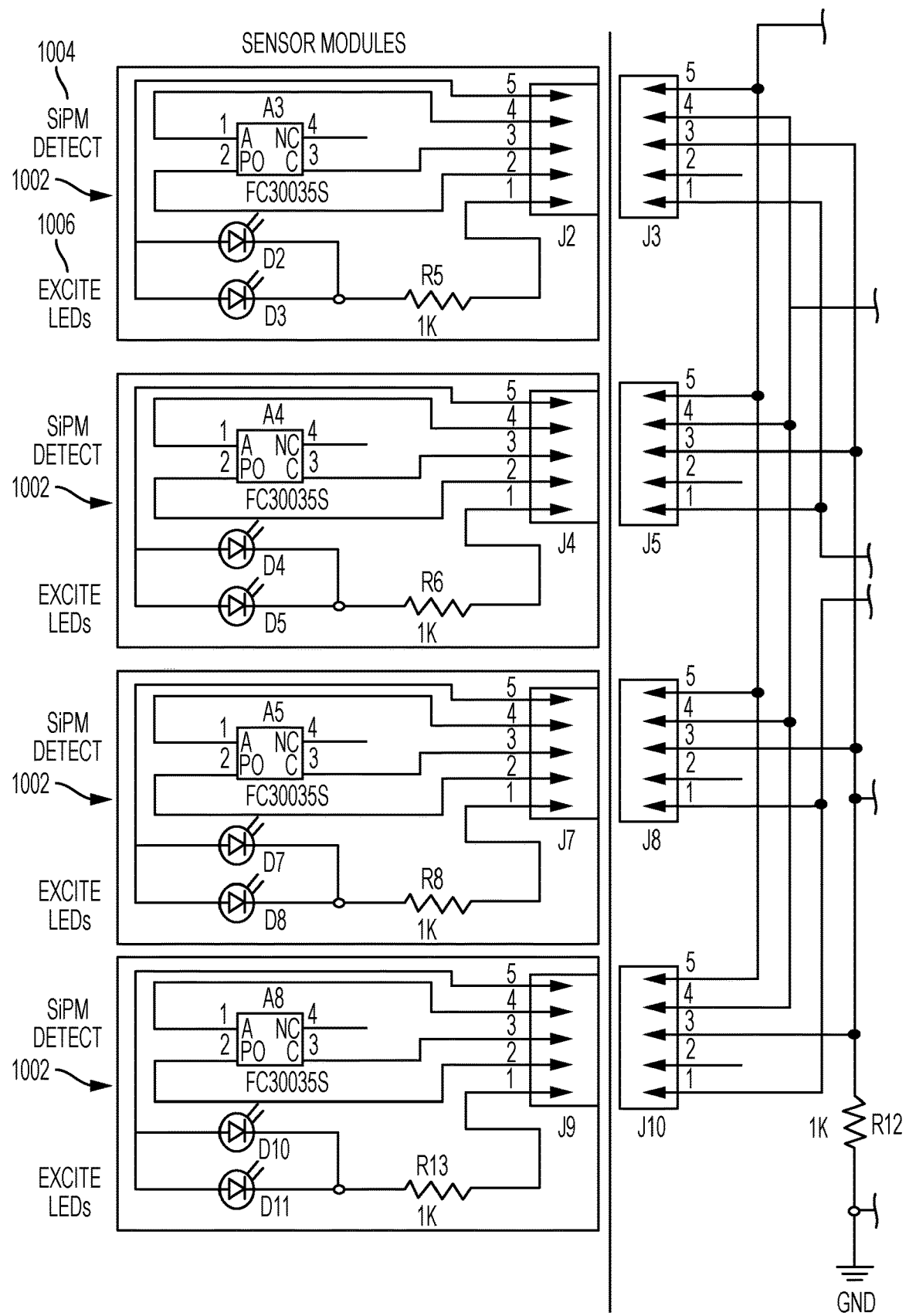
FIG. 10 illustrates another aspect of a device for determining analytes as shown and described herein.
Figure 10:
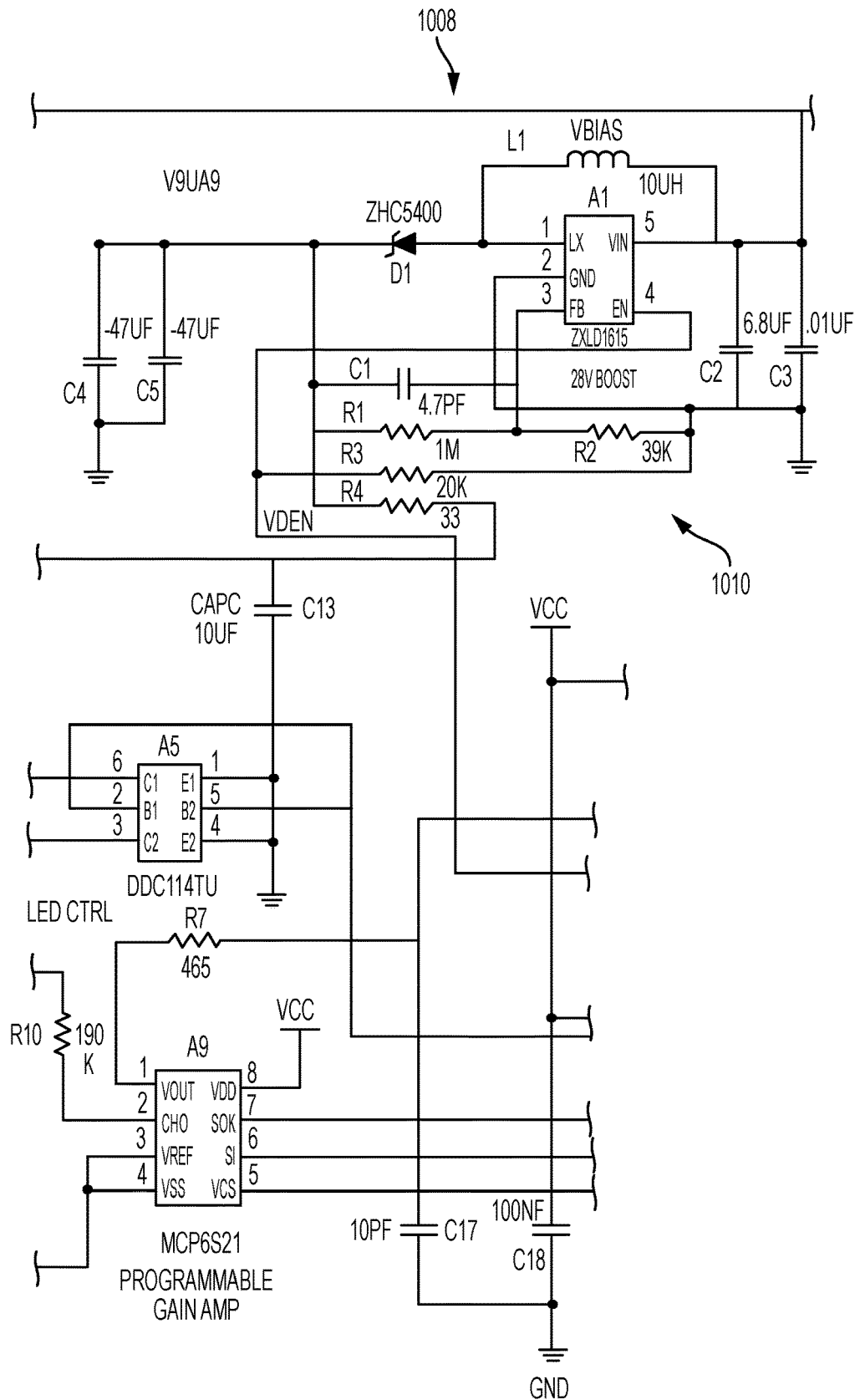
Figure 10:
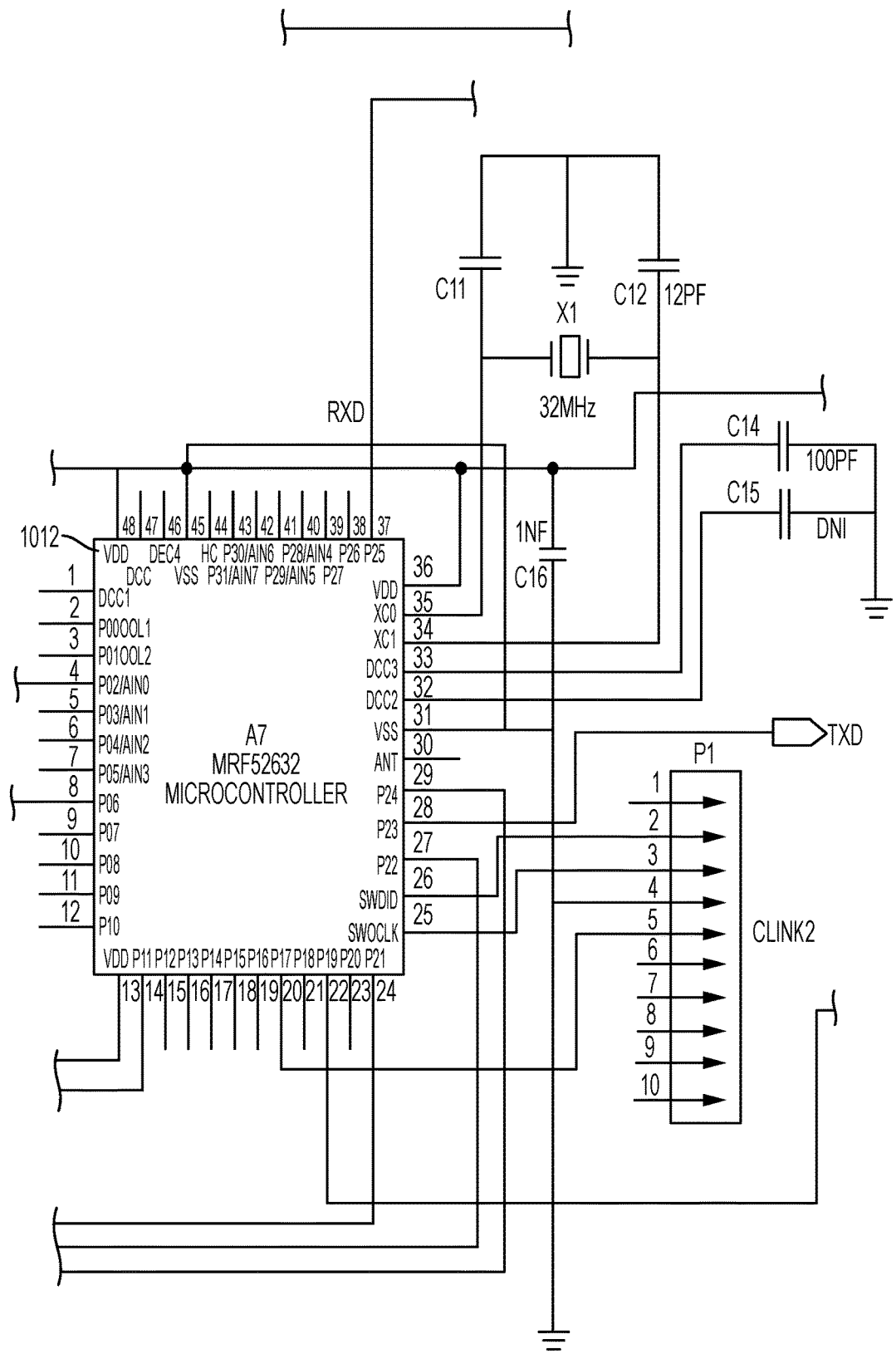
Figure 10:
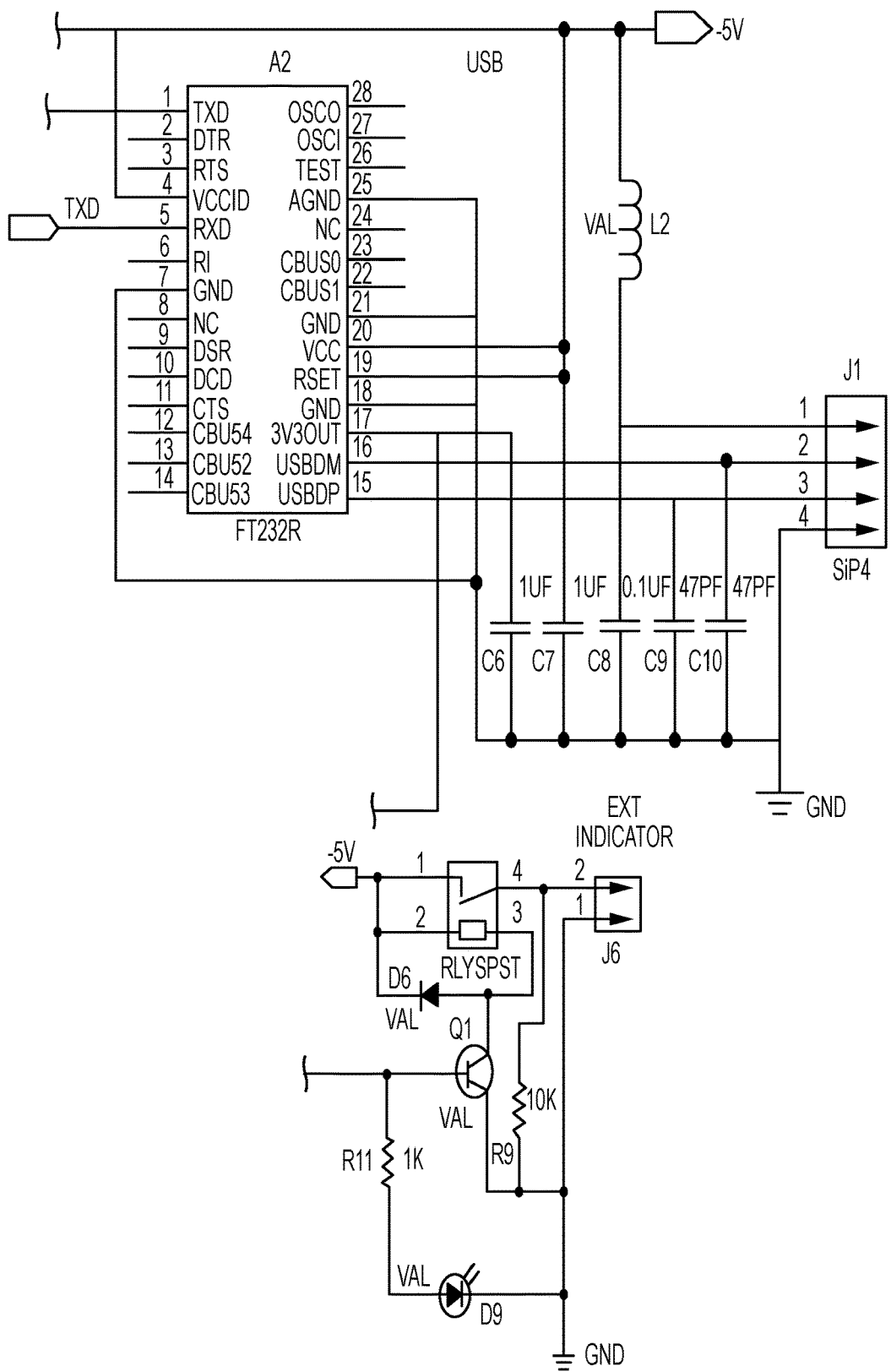

Referring now to FIG. 10, an example circuit diagram is provided. In this embodiment, each sensor module 1002 contains circuitry for SiPM detection 1004 and excitation 1006. These modules 1002 communicate with the printed circuit board controller board 1008 circuitry 1010, which has a microcontroller 1012 and other components configured to detect and communicate optical characteristics as described herein.

Figure 11:
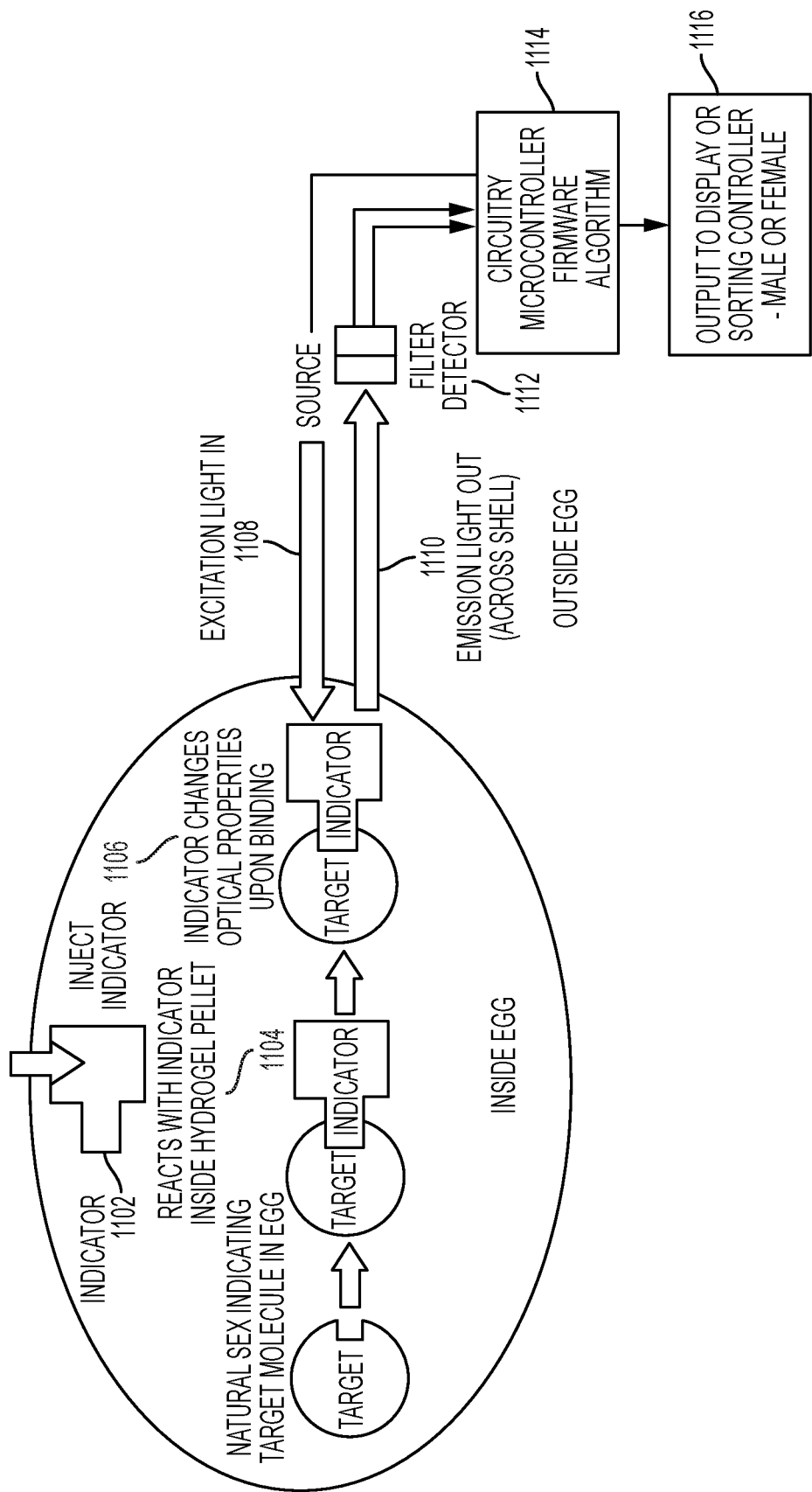
FIG. 11 illustrates another aspect of a method for determining analytes as shown and described herein.

Referring now to FIG. 11, a method of detection is shown. In step 1102 of method 1100, an indicator is injected into an egg. In step 1104 of method 1100, the indicator reacts with a natural sex indicating target molecule within the egg. In step 1106 of method 1100, the indicator changes optical properties upon binding to the target molecule.

In step 1108 of method 1100, excitation light is emitted into the egg by one or more LED emitters. In step 1110 of method 1100, the excitation light is received by the indicator and the indicator emits light out of the egg.

In step 1112 of method 1100, the indicator emission light is detected by one or more detectors. In step 1114 of method 1100, the one or more detectors sent emission light data to a printed circuit board controller. In step 1116 of method 1100, the printed circuit board controller determines whether the emission light data corresponds to a male of female embryo.

The most immediate benefit of the invention is to allow the sex determination of the egg weeks before it hatches. This will include direct benefit and financial savings of incubator space, energy savings, hatchery production area, and eliminate the widespread ethical concerns regarding killing of day old male baby chicks.

Further benefits include the possibility to improve QC of breeding eggs and clean eggs (human and veterinary vaccine industry) by identifying advantageous disease agents in them. The invention can also analyze and indicate other markers that may be configured for other analytes of interest within an egg including health and viability, potential diseases, or others by configuring the injectable element with an appropriate (one or more) indicator.

The egg pellet indicator will be substantially nontoxic as a simple hydrogel at very small displacement volume and comprised of as much as 80% water, with an indicator concentration below any possible de minimus threshold thereby potentially allowing the alternative consumption of the rejected male eggs in prepared feed and animal food mixes and possibly human consumption following extensive tox testing. If these objectives are met, potential costs can be cut approximately 40-50% and market opportunity increase by enabling a 40-50% efficient operation to increase to nearly 90% or more.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A device for detecting a presence or concentration of an analyte in or on an egg, said device comprising:
    a. an emitter, wherein said emitter is configured to emit light into or onto said egg;
    b. a detector, wherein said detector comprises a silicon photomultiplier and is configured to detect light emitted from a photoluminescent indicator molecule in or on said egg;
    c. a device body configured to hold said detector and said emitter in the vicinity of said egg; and
    d. a controller configured to analyze a change in a detectable quality of said indicator molecule based on said presence or concentration of said analyte,
    wherein the change in detectable quality comprises a change in luminescent lifetime.

2. The device of claim 1, wherein said device body comprises an enclosed chamber configured to encase said egg or an open cylinder configured to surround said egg.

3. The device of claim 2, wherein said enclosed chamber comprises an outer housing.

4. The device of claim 3, wherein said outer housing comprises a polymer.

5. The device of claim 2, wherein said enclosed chamber comprises an inner liner.

6. The device of claim 5, wherein said inner liner comprises aluminum.

7. The device of claim 6, wherein said aluminum has a mirror polish.

8. The device of claim 1, wherein said device body comprises a hand-held wand configured to allow a user to position said emitter and said detector to a position at an outer surface of said egg to perform said detection.

9. The device of claim 1, wherein said controller is a computer.

10. The device of claim 1, wherein said emitter comprises a light emitting diode.

11. The device of claim 1, wherein said analyte is located on an outer surface of said egg.

12. The device of claim 1, wherein the indicator molecule comprises a chromophore which is a long lifetime chromophore.

13. The device of claim 1, wherein the analyte is present in allantoic fluid within in the egg.

14. The device of claim 1, wherein the egg is a chicken egg.

15. The device of claim 1, wherein the indicator molecule has an expected luminescent lifetime range between about 100 and about 300 microseconds.

16. A method for detecting a presence or concentration of an analyte in or on an egg, said method comprising:
   a. introducing into or onto said egg ana photoluminescent indicator molecule having a detectable quality that changes when said indicator molecule is exposed to said analyte; and
   b. measuring any change in said detectable quality to thereby determine said presence or concentration of said analyte in or on said egg,
   wherein the change in detectable quality comprises a change in luminescent lifetime.

17. The method of claim 16, wherein said indicator molecule in said egg is exposed to one or more wavelengths of light matched to said absorbance of said indicator from a light source.

18. The method of claim 17, wherein said indicator molecule emits a luminescent signal after said exposure.

19. The method of claim 18, wherein said emitted luminescent signal is detected by at least one detector.

20. The method of claim 19, wherein said light source comprises a light emitting diode.

21. The method of claim 16, wherein said presence or concentration of said analyte is used to determine a condition comprising sex, health, or viral status.

22. The method of claim 16, wherein said analyte is located on an outer surface of said egg.

23. The method of claim 16, wherein the indicator molecule comprises a chromophore which is a long lifetime chromophore.

24. The method of claim 16, wherein the analyte is present in allantoic fluid within the egg.

25. The method of claim 16, wherein the egg is a chicken egg.

26. The method of claim 16, wherein the indicator molecule has an expected luminescent lifetime range between about 100 microseconds and about 300 microseconds.

* * * * *